United States Patent
Rancic et al.

(10) Patent No.: US 10,401,271 B2
(45) Date of Patent: Sep. 3, 2019

(54) METHOD AND DEVICE FOR DETERMINING THE WEAR OF A CUTTING TOOL FLANK

(71) Applicant: SNECMA, Paris (FR)

(72) Inventors: Mickael Rancic, Courcouronnes (FR); Nicolas Batista, Vert le Petit (FR); Damien Hebuterne, Breux-Jouy (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 227 days.

(21) Appl. No.: 15/038,200

(22) PCT Filed: Nov. 26, 2014

(86) PCT No.: PCT/FR2014/053036
§ 371 (c)(1),
(2) Date: May 20, 2016

(87) PCT Pub. No.: WO2015/079164
PCT Pub. Date: Jun. 4, 2015

(65) Prior Publication Data
US 2016/0290906 A1 Oct. 6, 2016

(30) Foreign Application Priority Data

Nov. 29, 2013 (FR) .................................... 13 61840
Nov. 29, 2013 (FR) .................................... 13 61859

(51) Int. Cl.
*G01N 3/56* (2006.01)
*G01N 3/58* (2006.01)
(52) U.S. Cl.
CPC .................. *G01N 3/56* (2013.01); *G01N 3/58* (2013.01)

(58) Field of Classification Search
CPC ...... G05B 19/4065; G05B 2219/37206; G05B 2219/50203; G05B 2219/37434; G01B 11/08; G01B 11/24; G01B 11/2433; G01B 11/12
See application file for complete search history.

(56) References Cited

U.S. PATENT DOCUMENTS

| | | | | |
|---|---|---|---|---|
| 4,744,242 A | * | 5/1988 | Anderson | B23Q 17/0947 340/683 |
| 5,825,017 A | * | 10/1998 | Pryor | F02F 1/24 250/208.1 |
| 2008/0161959 A1 | * | 7/2008 | Jerard | G05B 19/4065 700/110 |

OTHER PUBLICATIONS

International Search Report dated Feb. 24, 2015 in PCT/FR2014/053036, filed Nov. 26, 2014.
K. Glass et al. "Real-Time Tool Wear Estimation Using Cutting Force Measurements", Proceedings of the 1996 IEEE International Conference on Robotics and Automation, vol. 4, Apr. 22, 1996, pp. 3067-3072.
Yung-Chang Yen et al. "Estimation of Tool Wear in Orthogonal Cutting Using the Finite Element Analysis", Journal of Materials Processing Technology, vol. 146, No. 1, Jan. 1, 2004, pp. 82-91.

(Continued)

*Primary Examiner* — Elias Desta
(74) *Attorney, Agent, or Firm* — Oblon, McClelland, Maier & Neustadt, L.L.P.

(57) ABSTRACT

A method of determining the wear of a flank of a cutter tool, in which the wear is determined by a general function calculating a characteristic length of the wear as a function of at least one variable that depends on time, is provided.

10 Claims, 4 Drawing Sheets

(56) References Cited

OTHER PUBLICATIONS

I. N. Tansel et al. "Tool Wear Estimation in Micro-Machining. Part I: Tool Usage-Cutting Force Relationship", International Journal of Machine Tools and Manufacture, vol. 40, Jan. 1, 2000, pp. 599-608.
Vishal S. Sharma et al. "Cutting Tool Wear Estimation for Turning", Journal of Intelligent Manufacturing, vol. 19, No. 1, Jul. 3, 2007, pp. 99-108.

* cited by examiner

METHOD AND DEVICE FOR DETERMINING THE WEAR OF A CUTTING TOOL FLANK

FIELD OF THE INVENTION

The present description relates to a method of determining the wear of a cutter tool flank, and to a device enabling such a method to be performed.

BACKGROUND

Figure 1A:
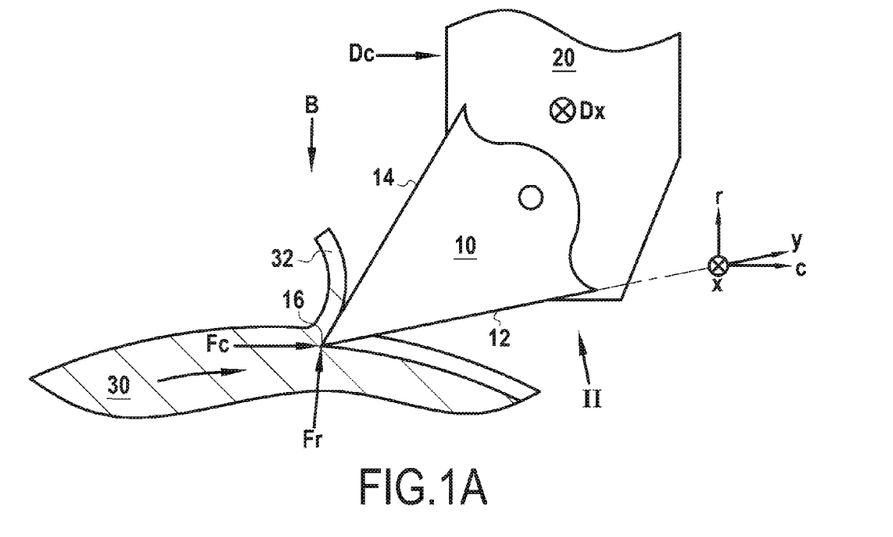
FIG. 1A, described above, shows a cutter tool while machining.
Figure 1B:
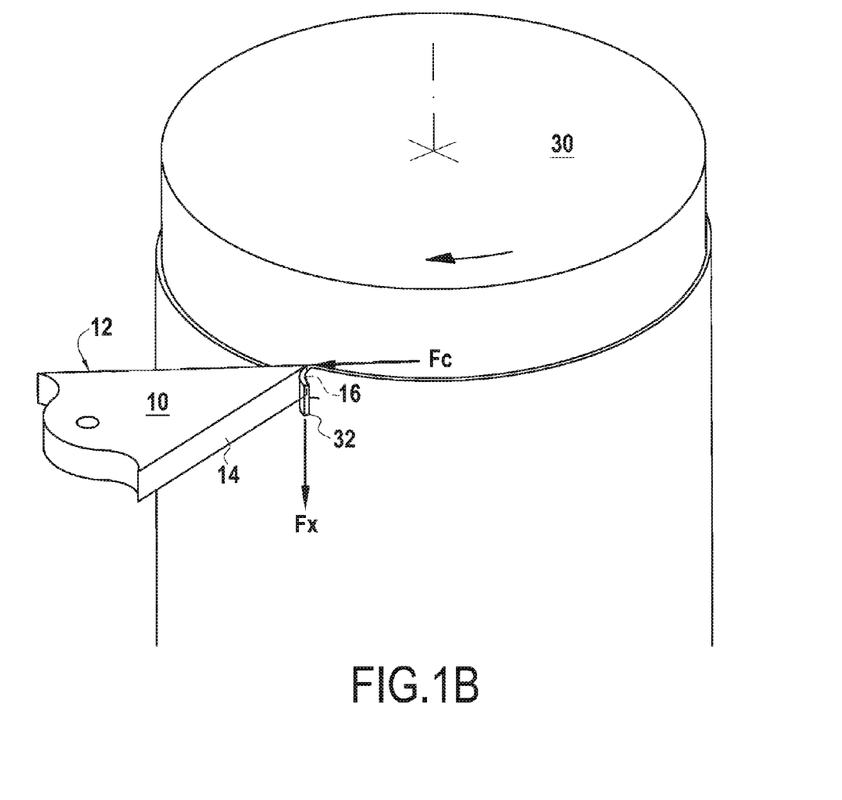
FIG. 1B, described above, is a perspective view looking along direction B in FIG. 1A.

When machining a part with a cutter tool, the cutter tool becomes progressively worn. FIG. 1A shows an example of a cutter tool 10 mounted on a machining tool 20 for machining a part 30. Specifically, the part 30 is a body of revolution and it rotates about its axis, while the machining tool moves with feed movement Dx along the direction of said axis in order to travel along the entire part 30. FIG. 1B is a perspective view of the part 30 and of the cutter tool 10 seen looking along direction B in FIG. 1A. Relative to the cutter tool 10, the part 30 thus follows a helical path that is characterized by a cutting speed Vc and a feed fz per revolution per tooth (helical pitch, if f is the overall feed per revolution and Z is the number of teeth, then f=fz×Z). Another machining parameter that is often used is the depth of cut (depth of material removed during cutting).

In general manner, when machining a part with a cutter tool, material is removed by the combination of relative movements between the part and the cutter tool: the cutting movement Dc in the direction c along which the cutting force Fc acts, and the feed movement Dx in the direction x along which the feed force Fx acts. The radial force Fr acts in a direction r perpendicular to the cutting direction c and to the feed direction x. These movements and forces are shown in FIGS. 1A and 1B. In the case of turning, i.e. when the part for machining is substantially a body of revolution rotating about its axis, as in the example of FIGS. 1A and 1B, the cutting direction c and the feed direction x correspond respectively to a tangential direction and to an axial direction, with the direction r being a radial direction.

In the example shown, the cutter tool 10 has a cutting edge 16, a face 14 (cut face), and a flank 12. The face 14 is the face along which the swarf 32 resulting from cutting the part 30 is removed. The flank 12 is the face situated facing the machined surface of the part 30. The cutting edge 16 lies at the intersection between the face 14 and the flank 12. Inserting the cutting edge 16 into the part 30 creates swarf 32.

Figure 2:
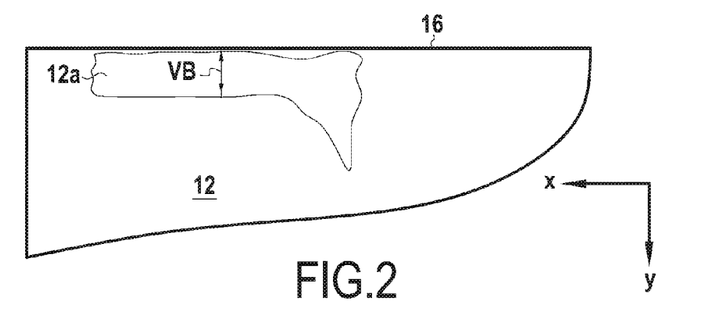
FIG. 2, described above, is a view of the flank of the FIG. 1 actuator looking along direction II in FIG. 1.

As can be seen in FIG. 2, which shows the flank 12 of the cutter tool 10 seen looking along direction II in FIG. 1A, the flank 12 has a wear zone 12a that appears and grows as the tool 10 is being used. The wear of the flank 12 may be due essentially to the high mechanical stresses that result from the part 30 rubbing against the cutter tool 10. The wear zone 12a on the flank is generally in the form of a shiny striped strip parallel to the cutting edge.

With reference to FIG. 2, an abscissa axis is defined by the feed direction x and parallel to the initial cutting edge 16, i.e. parallel to the cutting edge 16 before it has been subjected to any wear. An ordinate axis y is also defined that is perpendicular to the feed direction x in the plane of the flank 12. The wear zone 12a of the flank 12 may be characterized at each abscissa value x, by a characteristic length written VB(x) (or more simply VB) and referred to as flank wear. Flank wear VB is generally measured in millimeters (mm). As shown in FIG. 2, the flank wear VB(x) is the distance, at a given abscissa value x, between the initial cutting edge 16 and the point of the wear zone 12a that is furthest from the initial cutting edge 16, measured along the direction of the ordinate axis.

Instead of the characteristic length VB, it is known to characterize the wear of the flank by a characteristic length VBmax referred to as the maximum flank wear and calculated as being the maximum of the flank wear VB(x) over all of the abscissa values x. In order to avoid edge effects, the maximum flank wear may be calculated over only a central portion of the wear zone 12a of the flank. The extent of said central portion may be determined using criteria that are standardized and known to the person skilled in the art.

When the wear of a cutter tool reaches a level that is excessive, the cutter tool can deform, crack, or indeed flake, thereby causing scraps to become inserted in the machined part. Furthermore, damage to a tool leads to an increase in forces and in vibration during machining, which is harmful for the quality of the machined part, i.e. for its geometrical and dimensional characteristics, for its surface state, and for the integrity of its material. It is therefore essential to monitor the cutter tool and to discard it when its wear, and in particular its flank wear, becomes excessive and exceeds a certain threshold, referred to as the discard criterion.

In order to determine whether the flank wear of a tool is excessive, a method is known of monitoring flank wear on the basis of at least one other magnitude (referred to below as the "observed magnitude A"). Such magnitudes (or physical quantities) may include a power or a force exerted by the cutter tool on the part. When the observed magnitude exceeds a threshold As, machining is stopped and the cutter tool needs to be changed. The threshold As needs to be determined beforehand, during a predetermining step, as a function of the parameters of the machining.

Figure 3:
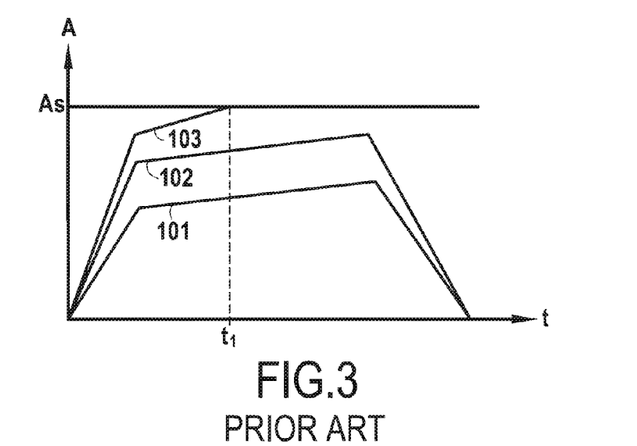
FIG. 3, described above, is a diagram showing a prior art method using an observed magnitude f determining wear in indirect manner.

An example of such a method is shown diagrammatically in FIG. 3, in which curves 101, 102, and 103 represent the variation in an observed magnitude A as a function of machining time t during three respective successive machining operations. As can be seen on curve 101, the observed magnitude A increases steeply at the beginning of a first machining operation (stage in which the cutter tool penetrates into the part), and then increases more slowly, and finally decreases when the tool is removed from the part and the first machining operation comes to an end. The curve 102 shows a second machining operation having substantially the same appearance as the curve 101 representing the first operation, except that the observed magnitude A reaches higher values as a result of the wear of the cutter tool. During a third machining operation, the values reached by the observed value A (which varies as represented by curve 103) are even higher, such that during the third operation, the observed magnitude A reaches the predetermined threshold As and the third operation is stopped at time t=t1.

A major drawback of such a method is the time required by the steps for predetermining the threshold As for the observed magnitude A. Specifically, insofar as the discard criterion is often expressed relative to flank wear, determining a threshold As requires correspondence to be established empirically between flank wear and the observed magnitude A, which requires a large number of machining operations.

Furthermore, although the flank wear of a tool is a magnitude that is intrinsic to the tool, the observed magnitude A, such as a force or a power, generally depends on the part being machined, and in particular on its material, on the cutting speed, and on all of the machining parameters. With such a method, a threshold thus needs to be predetermined in full once again for each machining operation and for each change of a parameter.

In addition, when the observed magnitude A has reached the predetermined threshold As, the tool is changed, but the value of the flank wear of that tool is still not known. For example, a tool may have suffered premature wear, such that the observed magnitude reaches its threshold long after the flank wear has reached a discard criterion. Under such circumstances, since the tool has been used beyond its discard criterion, the quality of machined parts may not satisfy fabrication specifications.

There therefore exists a need for a new type of method for determining the wear of a cutter tool.

SUMMARY OF THE INVENTION

The present description provides a method for determining the wear of a flank of a cutter tool, wherein said wear is determined by means of a general function calculating a characteristic length of said wear as a function of at least one variable representative of operating conditions of machining performed by the cutter tool, the method comprising the steps of:
  calculating a first value of said characteristic length by a first function;
  calculating a second value of said characteristic length by a second function; and
  calculating said general function as the maximum of said first value and said second value.

For example, the characteristic length of said wear may be the flank wear VB or the maximum flank wear VBmax, as defined above. The variables representative of the operating conditions during machining may be variables that depend on time and, among other possibilities, they may be selected from: time itself; observed length of cut; another variable representative of the machining feed over time; or indeed a force exerted by the tool on the part; an energy; a power; or a torque. Thus, the proposed method enables variation in the characteristic length to be monitored as a function of variation in magnitudes obtained while machining. In addition, the general function may be incorporated in a longer chain of calculations, such that characteristic length is merely an intermediate magnitude used for determining some other magnitude.

The variables representative of operating conditions during machining may also be variables that vary in predetermined manner, e.g. the length of cut (as planned rather than observed) or indeed the machined length Lu, the diameter of cut Dc, the feed speed Vf, and magnitudes that are related therewith. Under such circumstances, the proposed method makes it possible in predictive manner to determine the variation in the characteristic length of flank wear as a function of planned machining conditions. Unlike models of the Taylor or Gilbert type, which serve to determine the machining time that corresponds to given flank wear and which require the constants of the model to be re-evaluated for different flank wear, the method of the invention provides the length characteristic of the wear for all values of said representative variable, e.g. for all values of the length of cut, i.e. by using a given general function.

Under all circumstances, the method proposed in the present description makes it possible to determine directly the flank wear of the tool by calculating a length that is characteristic of said wear. The method thus calculates a magnitude that is intrinsic to the tool, thereby avoiding passing via some other magnitude and determining a threshold for that other magnitude, which threshold would be valid only for one part and one set of machining parameters. Furthermore, said characteristic length, in particular for flank wear VB, provides a direct measurement of the wear of the flank of the tool. The wear of the flank is thus known and can be compared directly with a discard criterion that is intrinsic to the tool.

In addition, in such implementations, two different functions are used for modeling the variation in the characteristic length as a function of the time-dependent variable. The general function is then the maximum of the first function and the second function, which has the advantage of being conservative: the flank wear is thus never underestimated, and there is no risk of believing a tool to be healthy even though its flank wear has in fact exceeded the discard criterion.

In certain implementations, said wear is determined in real time. Wear is thus determined without waiting, progressively as the calculation is performed by the general function while the tool is machining. Real time determination can provide a value for the characteristic length at any instant and as soon as the value is available. Thus, when the determination method is used for monitoring purposes, it makes it possible in real time to know how much the tool has worn, and, where appropriate, to take appropriate measures in real time based on said wear, e.g. stop machining if the characteristic length exceeds a discard criterion.

In certain implementations, said general function depends on constants determined by machining tests. More particularly, in certain implementations, the first function and/or the second function depends on constants determined by machining tests. Such a function, that depends both on constants that are determined by machining tests and on variables, is sometimes known as a semi-empirical function. Thus, even though machining tests are necessary in order to calibrate the function, much less testing is needed than in prior art methods, and the function that is obtained remains valid for several sets of parameters.

In certain implementations, the characteristic length for the wear of the flank is calculated as a function of cutting speed (Vc), feed per revolution and per tooth (fz), depth of cut (ap), cutting energy (Ec), and radial force (Fr). These variables are well known to the person skilled in the art. It should be recalled that the energy associated with a force is linked to the work done by said force. Furthermore, the dependency on the cutting energy may be presented in the form of dependency on the accumulated cutting energy, as described in detail below.

Among the above-mentioned variables, the radial force Fr exerted by the cutter tool on the part and the cutting energy Ec still depend on time, in the sense that they vary from one instant to another. Depending on circumstances, the other variables may or may not depend on time. Specifically, some of the parameters selected from the cutting speed Vc, the feed per revolution and per tooth fz, and the depth of cut ap are generally setpoints, however the setpoints may be constant or they may vary as a function of time.

In such implementations, the general function makes use only of variables that are known to the machining tool, and that are easily accessible using conventional measurement means. Such a general function is thus particularly simple to calculate without requiring any major change to the instrumentation of the machining tool.

As mentioned above, in certain implementations, the variable representative of the operating conditions of machining performed by the cutter tool is a time-dependent variable. In certain other implementations, the variable representative of the operating conditions of machining performed by the cutter tool is a predetermined variable, i.e. a variable for which the variation, or at least one future value, is known as a function of the desired machining results.

For example, the length of cut may be selected as the representative variable in both situations. In the first situation, the length of cut as a time-dependent variable is the length of cut that is actually observed during machining; the method is thus used as a monitoring method. In the second situation, the length of cut as a predetermined variable is the value of the necessary length of cut set by the machining requirements in order to obtain the desired result. This value is known before the machining is performed, and in this respect it is predetermined; the method is then used as a prediction method, serving to predict a characteristic length of flank wear as a function of the predetermined variable, specifically the length of cut.

In certain implementations, the first function depends on time t and the first function is of the form:

$$f1(Vc, fz, Ec, t) = 10^{A1} Vc^{B1} fz^{C1} Ecc^{D1}$$

where Vc is the cutting speed, fz the feed per revolution and per tooth, Ecc the accumulated cutting energy, and A1, B1, C1, and D1 are four constants. The accumulated cutting energy designates the cutting energy that is accumulated during machining, and more precisely:

$$Ecc(t) = \int_{t0}^{t} Ec(u) du$$

where t0 is the instant at which machining starts and t is the current instant. By way of example, the constants A1, B1, C1, and D1 may be determined during machining tests.

A first function of the above form is particularly advantageous for modeling certain stages of variation in flank wear.

In certain implementations, the second function depends on time t, and the second function is of the form:

$$f2(Vc, fz, Fr, t) = 10^{A2} 10^{[B2 + C2 \, log(fz) + D2 \, log(Vc)] \cdot log(Frc)}$$

where Vc is the cutting speed, fz the feed per revolution and per tooth, Frc the accumulated radial force, and A2, B2, C2, and D2 are four constants. The accumulated radial force is the radial force as accumulated during the machining, and more precisely:

$$Frc(t) = \int_{t0}^{t} Fr(u) du$$

where t0 is the instant at which machining starts and t is the current instant. By way of example, the constants A2, B2, C2, and D2 may be determined during machining tests.

A second function of the above form is particularly advantageous for modeling certain stages of variation in flank wear, in particular stages other than those that are already modeled well by the first function.

In certain implementations, the first function depends on cutting length Lc and the first function is of the form:

$$f1(Vc, fz, Lc) = 10^{A1} Vc^{B1} fz^{C1} Lc^{D1}$$

where Vc is the cutting speed, fz the feed per revolution and per tooth, Lc the cutting length, and A1, B1, C1, and D1 are four constants. By way of example, the constants A1, B1, C1, and D1 may be determined during machining tests. If a predictive value is given to the length of cut, as contrasted to a time-dependent value, none of the variables depends on time nor on magnitudes that are measured during machining. Thus, a first function of the above form is particularly advantageous for predictive modeling of certain stages in the variation of flank wear. In addition, the predictive model makes it possible, with few tests, to draw up charts of constant flank wear for the part as a function of these parameters taken together. Knowing the discard criterion and the desired value for the length of cut Lc, it is thus possible to select the cutting conditions that are the most effective, while not exceeding the discard criterion. This makes it possible in particular to shorten the time required for machining.

In certain implementations, in particular for turning, the first function also takes account of the depth of cut ap, e.g. by multiplying the form given above for the first function f1 by the depth of cut to a certain power (f1×ap$^{E1}$).

The present description also provides a computer program including instructions for executing steps of the determination method as described above when said program is executed by a computer.

The present description also provides a computer readable data medium including a computer program comprising instructions for executing steps of the determination method as described above.

The present description also provides a device for determining the wear of a flank of a cutter tool for machining a part, the device having means for determining a characteristic length of said wear, said determination means taking account of at least one variable representative of the operating conditions of machining performed by the cutter tool, and said determination means being configured to:
calculate a first value of said characteristic length by a first function;
calculate a second value of said characteristic length by a second function; and
calculate said characteristic length as the maximum of said first value and said second value.

In certain implementations, the determination device includes means for measuring the cutting energy of the tool or the radial force exerted by the tool on the part, as a function of time. The measurement means may be suitable for taking instantaneous measurements.

The present description also relates to a method of determining the flank wear of a cutter tool, in which said wear is determined by means of a predetermined explicit general function that calculates a characteristic length of said wear as a function of at least one variable representative of the operating conditions of machining performed by the cutter tool. The general function is explicit, i.e. it is in the form of a mathematical expression that gives the characteristic length directly as a function of other variables, as contrasted in particular to functions that are implicit, that do not have a direct expression, and/or that require digital resolution. The general function is predetermined, i.e. it is of a form that is known in feed, as contrasted to interpolations or to systems of the artificial neural network type. Thus, the predetermined explicit general function presents the advantage of being robust, fast, and easy to perform, and of not requiring a training stage or any sophisticated solving means. In addition, even if the predetermined explicit general function depends on constants that are determined by machining tests, only a few tests are necessary for determining these constants (about ten tests), which is much less than the number of tests required for establishing a training database for an artificial neural network (several hundreds of tests). Furthermore, the necessary tests can be optimized by using the Taguchi method.

Figure 5:
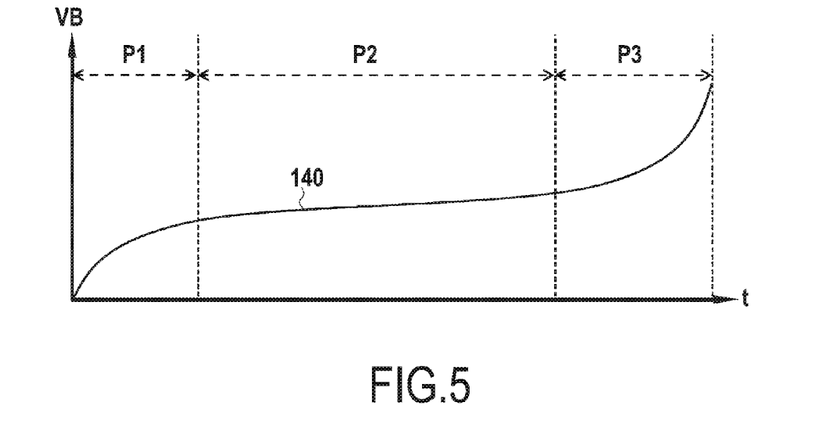
FIG. 5, described above, is a diagram showing how the flank wear VB varies as a function of cutting time.

Furthermore, it is known from experience that the flank wear VB of a cutter tool varies as a function of cutting time t in a manner that has the appearance shown diagrammatically in FIG. 5. On the curve 140, there can be seen three successive stages in the variation of flank wear VB. During a first stage P1, the curve 140 is substantially concave and flank wear increases strongly. This first stage P1 is referred to as an initiation stage, and it corresponds to running in the cutter tool. Thereafter, the flank wear VB enters a second stage P2, referred to as a linear stage, in which it increases in substantially linear manner and less strongly than during the first stage P1. Finally, in a third stage P3, the flank wear enters a stage known as the catastrophic stage. In this third stage P3, the curve 140 is substantially convex and flank wear increases very strongly.

In order to determine whether the flank wear of a tool is excessive, there is a known method of monitoring the flank wear already described with reference to FIG. 3.

However, such a method does not make it possible to know whether the flank wear of the cutter tool has or has not entered into a stage of catastrophic increase. Unfortunately, once it enters into a stage of catastrophic increase in flank wear, the flank of the cutter tool can become degraded very quickly and can damage the part being machined.

There thus exists a need for a novel method of evaluating the wear of a cutter tool.

The present description also relates to a method of evaluating the wear of a flank of a cutter tool, the method being characterized in that:

during machining of a part by the cutter tool, at least one magnitude representative of a force or a movement of the cutter tool relative to said part is measured in real time; and the beginning of a stage of catastrophic increase in said wear is determined by detecting a sudden change in the overall variation of said at least one magnitude as a function of time.

A magnitude representative of a force or a movement is a magnitude having variation that tracks or is indicative of the variation of the force or the movement. The representative magnitude may be the force or the movement itself. Alternatively, or in addition, the representative magnitude may be obtained by calculation on the basis of the force or the movement, e.g. by operations of differentiation or integration, or by applying a filter. When applying a filter, the purpose of the filtering may be to smooth the magnitude, to eliminate noise, to exacerbate variations in the magnitude, or some other purpose, in particular in order to obtain the overall variation in the magnitude. The representative magnitude may also be a magnitude that is correlated with the force or the movement, in a manner that is implicit or explicit. The representative magnitude is not just any magnitude, it is not a mere parameter of the machining environment. The representative magnitude is a magnitude that gives information about the variation of the machining, i.e. it is a magnitude that varies in a manner that is impacted by the machining. Thus, a magnitude representative of a force or of a movement could be constituted, amongst others, by: a speed; an acceleration; an energy; a power; a torque; vibration; a temperature (in particular the temperature in the vicinity of the cutting edge); an electric current (e.g. the current controlling the cutter tool); a voltage; an acoustic measurement signal; etc.; or indeed a magnitude that is obtained from at least one of the preceding magnitudes by calculation, for example.

Measuring a magnitude in real time means that the magnitude is measured without waiting, progressively as this magnitude varies during the machining. Real time measurement can provide a value for the measured magnitude at any instant and as soon as the value is available. The magnitude may be measured continuously or otherwise. When it is measured in discrete manner, the frequency of measurement needs to be sufficiently high to keep track accurately of the variation in the magnitude.

The overall variation of a magnitude is information about slow variations in the magnitude, i.e. information that is representative of, or a function of, the variation in only the mean value of the magnitude and possibly variation in its lowest frequency harmonics. For example, this information is calculated over a time interval of sufficient amplitude to reveal the slow variations in the signal. The overall variation may be a smoothed or averaged value of the magnitude. The overall variation of a magnitude, as contrasted to the magnitude itself, does not have rapid fluctuations, regardless of whether such rapid fluctuations are measurement noise or are representative of vibration of the cutter tool and/or of the part. In particular, the overall variation is free of rapid fluctuations that are uniform throughout measurement of the magnitude, or during a useful portion of that measurement.

A sudden change in the overall variation of a magnitude is a change that can be characterized by a remarkable point: an extremum, a slope breakpoint, a point of inflection, a singularity, a discontinuity, etc. A sudden change may be the result of an increase or a decrease in the overall variation of the observed magnitude.

The inventors of the present invention have observed that during the machining of a part there exists a correlation between a sudden change in the overall variation of a magnitude representative of a force or a movement of the cutter tool relative to the part and the flank wear VB characteristic of the wear of the cutter tool entering into a stage of catastrophic increase. The method of the present description takes advantage of this correlation to determine when a catastrophic stage in the increase of flank wear of a cutter tool begins. By means of such a method, it is possible to know the instant of entry into the catastrophic stage. As a function of this instant, it is possible to stop machining before the flank wear of the cutter tool becomes prejudicial for the shape or the integrity of the part. The cutter tool can be changed before damage is observed in the machined part.

Furthermore, such a method does not require a step of determining a threshold. It can therefore be applied simply and quickly.

In certain implementations, the sudden change is a break of slope. The step of determining the beginning of the catastrophic stage is thus performed by detecting a slope breakpoint in the curve for the overall variation of the magnitude, which reveals a sudden change in the overall variation of said magnitude. It should be recalled that a slope breakpoint is a point between two substantially affine portions (or two portions of substantially affine overall variation) of a curve, the two portions having different slopes. In the context of the present method, a slope breakpoint is an element that is easy to detect and, without ambiguity, it provides an indication that variation of the measured magnitude has intensified.

In certain implementations, the sudden change is a point of inflection. The step of determining the beginning of the catastrophic stage is thus performed by detecting a point of inflection in the curve for the overall variation of the magnitude, which is representative of a sudden change in the overall variation of said magnitude. It should be recalled that a point of inflection is a point on a curve where the curve crosses its tangent.

In certain implementations of the above-described method:
while machining a part by means of the cutter tool, at least two magnitudes are measured that are representative of a force or a movement of the cutter tool relative to said part; and
the beginning of a stage of catastrophic increase in said wear is determined by detecting a sudden change in the overall variation of at least two of said magnitudes as a function of time.

On the basis of the overall variations of two magnitudes for determining the beginning of a stage of catastrophic increase in wear, such implementations of the method present redundancy that can make it possible to determine said beginning in a manner that is more reliable by limiting false determinations, i.e. determinations for which the overall variation of one magnitude is not consistent with the overall variation of other magnitudes; false determinations may be of various origins, including failures of measurement means or some other anomaly of the cutter tool or of the part.

In certain implementations, the magnitudes are selected between a force and a movement of the cutter tool relative to the part.

In certain implementations, the forces and movements are selected from: the cutting force exerted by the cutter tool on the part; the axial force exerted by the cutter tool on the part; the radial force exerted by the cutter tool on the part; the axial movement of the cutter tool relative to the part; and the cutting movement of the cutter tool relative to the part. Since some of these magnitudes are already measured while machining, it may be possible to apply the method without requiring any additional measurement means; such a method is thus found to be inexpensive.

In certain implementations, the beginning of the catastrophic stage is determined in real time. In such implementations, magnitude measurements are processed directly, progressively as they are acquired in real time. Thus, machining can be stopped before the flank wear of the tool has increased excessively and the tool has damaged the part being machined.

The present description also relates to a computer program including instructions for executing steps of the above-described evaluation method when said program is executed by a computer.

The present description also provides a computer readable data medium including a computer program comprising instructions for executing steps of the above-described evaluation method.

The present description also relates to a device for evaluating the flank wear of a cutter tool for machining a part, the device being characterized in that it comprises means for real time measurement of at least one magnitude representative of a force or a movement of the tool relative to the part during machining of said part by the tool, and means for determining the beginning of a stage of catastrophic increase in said wear, which means are configured to indicate the beginning of the stage of catastrophic increase in said wear by detecting a sudden change in the overall variation of said at least one magnitude as a function of time.

Such a device makes it possible to determine whether the cutter tool is in a stage of catastrophic increase in its flank wear, without any need to calculate thresholds for equivalent magnitudes.

BRIEF DESCRIPTION OF THE DRAWINGS

The invention and its advantages can be better understood on reading the following detailed description of implementations of the invention given as non-limiting examples. The description refers to the accompanying drawings, in which.

DETAILED DESCRIPTION OF THE INVENTION

In the implementation that is described below, the determination method of the invention is applied to a cutter tool of the above-described type for use in turning TA6V (the Ti Al 6 V alloy as named in the AFNOR French standard; AMS 4928 in the ASTM American standard). The wear of the flank of the cutter tool in this example is to be characterized by the maximum flank wear VBmax. Nevertheless, the present invention does not apply only to turning, nor does it apply only to TA6V, and it is possible to select a characteristic length other than the maximum flank wear VBmax.

Figure 4:
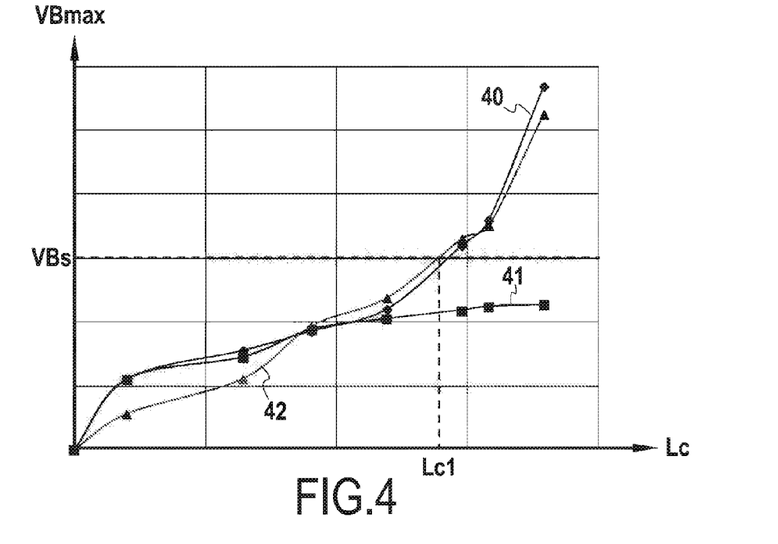
FIG. 4 shows how maximum flank wear varies as a function of the observed cutting length with examples of curves for the first and second functions used in the method constituting the subject matter of the present description.

FIG. 4 shows a curve 40 representative of the variation in maximum flank wear VBmax as a function of the observed length of cut Lc, i.e. the length of cut observed while machining and depending on time. The length of cut Lc is associated with the cutting time t by means of a formula that depends on the type of machining. By way of example, when turning, the following relationship applies:

$$Lc = \frac{Dc\pi Lu}{fz}$$

where Lu is the length machined in the feed direction (Lu=Vfxt, where Vf is the speed of feed and t is time). The length of cut Lc is thus a variable that depends on time. Expressing all magnitudes as a function of length of cut Lc rather than as a function of time t makes it possible in particular to avoid taking account of any interruptions in the performance of the machining.

Below, the term "point" is used of a curve to designate a point of one of the curves 40, 41, 42 that is represented by a symbol such as an upright square, a lozenge (a tilted square), or a triangle. Specifically, with this terminology, each of the curves 40, 41, 42 has eight points set out in the direction of increasing lengths of cut Lc (from left to right in FIG. 4). For curve 40, these points correspond to experimental measurements.

On curve 40, there can be seen three successive phases in the variation of maximum flank wear VBmax. During a first stage, between the first two points of the curve 40, the curve 40 is substantially concave and flank wear increases strongly. This first stage, referred to as the initiation stage, corresponds to running in the cutter tool. Thereafter, approximately between the second point and the fifth point, the maximum flank wear VBmax enters into a second stage referred to as the "linear" stage, in which it grows in substantially linear manner and less strongly than during the first stage. Finally, in a third stage, approximately between the fifth point and the eighth point, maximum flank wear enters into a stage known as a "catastrophic" stage. In this third stage, the curve 40 is substantially convex and the flank wear increases more strongly than in the linear stage.

The three above-described stages of variation are to be found in tests performed on other materials and/or with other types of machining.

In the present example, the curve 40 is obtained as a reference curve, by performing individual measurements using any prior art method. Furthermore, the method in an implementation of the invention is also applied to the present turning.

To do this, use is made of a first function f1 and of a second function f2 having the following respective forms:

$$f1(Vc,fz,Ec,t) = 10^{A1} Vc^{B1} fz^{C1} Ecc^{D1}$$

$$f2(Vc,fz,Fr,t) = 10^{A2} 10^{[B2 + C2\ log(fz) + D2\ log(Vc)] \cdot log(Frc)}$$

where Vc is the cutting speed, fz is the feed per tooth and per revolution, Ecc is the accumulated cutting energy, Frc is the accumulated radial force, and A1, B1, C1, D1, A2, B2, C2, and D2 are eight constants. The variables may be known (e.g. the cutting speed can be set, whether it be constant or variable), or else it can be measured using sensors.

The maximum flank wear VBmax depends on the history of cutting. The fact that accumulated magnitudes are used such as the accumulated radial force Frc or the accumulated cutting energy Ecc in the expressions for the first and second functions f1 and f2 represents taking into account this cutting history.

Furthermore, the accumulated cutting force (accumulated Fc) or the accumulated cutting torque could be used instead of the accumulated cutting energy Ecc in the expression for the first function f1. In addition, the accumulated axial force (accumulated Fx) could be used instead of the accumulated radial force Frc in the expression for the second function f2. Some or all of the constants A1, B1, C1, D1, A2, B2, C2, and D2 would need to be adapted accordingly. Beyond that, an arbitrary magnitude associated with such forces could be used in the functions f1 and/or f2. In non-limiting manner, such magnitudes include: energy; power; torque; control electrical current; control voltage (in particular for the spindle current); a temperature; vibration; any magnitude obtained from the above by mathematical operations (in particular differentiation and integration); etc.

In the first and second functions f1 and f2 of the present implementation, the depth of cut ap does not appear explicitly in the expressions for f1 and f2, but it has an influence on the forces and the energies; it is therefore taken into account indirectly via the accumulated cutting energy Ecc and the accumulated radial force Frc. Dependency on the depth of cut ap could nevertheless be explicit.

In the first and second functions f1 and f2, the dependency on time comes at least from the cutting energy Ec and the radial force Fr, both of which depend on time, and from the fact that the cutting energy Ec and the radial force Fr are integrated relative to time to give the accumulated cutting energy Ecc and the accumulated radial force Frc. The first and second functions f1 and f2 thus depend on time at least for these two reasons. Furthermore, the cutting speed Vc and the feed per revolution and per tooth fz may also depend on time.

The general form of the first function f1 serves to model the first and second stages of variation in maximum flank wear VBmax, as can be seen in FIG. 4. Specifically, the curve 41 representing the first function f1 coincides almost exactly over the initiation stage and the linear stage with the curve 40 representing the real variation in the maximum flank wear VBmax.

The general shape of the second function f2 serves to model the third stage of variation in maximum flank wear, as can be seen in FIG. 4. The curve 42 representing the second function f2 is very close in this third phase to the curve 40 representing the real variation in maximum flank wear VBmax.

The constants A1, B1, C1, D1, A2, B2, C2, and D2 can be determined by cutting tests, by varying the parameters Vc and fz, and by measuring Ecc, Frc, and VBmax. The person skilled in the art knows how to determine constants in this way. In the example of FIG. 4, the values of the eight constants A1, B1, C1, D1, A2, B2, 02, and D2 lie in the range 0 to 10 in absolute value. More precisely, in the example of FIG. 4, said constants may have approximately the following values: A1≈−5.2, B1≈1.5, C1≈0.6, D1≈0.3, A2≈−2.9, B2≈−0.74, C2≈−0.22, D2≈−0.68.

The maximum flank wear VBmax as a function of the length of cut Lc can thus be calculated by a general function f of the form: f=max(f1,f2), where f1 and f2 are the above-defined functions, which depend on time-dependent variables. It is thus possible from FIG. 4 to deduce that f=f1 over the initiation stage and over the linear stage approximately, and that f=f2 over the catastrophic stage, approximately. Taking the maximum of the first and second functions f1 and f2 for the general function f is not only conservative, but it also provides a model that matches experimental tests and that takes account of the variations in maximum flank wear during each of the three stages of variation.

In other configurations (in particular different materials and/or machining), functions other than f1 and f2 could be used in order to approximate the experimental results. Thus, the first and second functions f1 and f2 may have expressions that are different, in particular expressions that depend on time and constants that are determined experimentally. The first and second functions f1 and f2 could also be replaced by a single expression, in particular an expression including a maximum or a minimum function.

FIG. 4 shows a threshold VBs. In this example, the threshold VBs is a discard criterion for maximum flank wear, i.e. the cutter tool needs to be discarded as soon as its maximum flank wear VBmax exceeds the discard criterion VBs. In practice, VBs generally lies in the range 0.2 mm to 0.3 mm.

In the example of FIG. 4, the curve 42 representative of the second function f2 reaches the discard criterion VBs for a length of cut Lc1. The wear level of the cutter tool thus justifies stopping machining at the cutting length Lc1 in order to change the tool.

In the present implementation, the wear of the flank of the cutter tool, i.e. in this example the maximum flank wear VBmax as calculated by the general function f, is determined in real time. The maximum flank wear VBmax is thus calculated progressively during machining and the machining can be interrupted as soon as the discard criterion VBs is reached by the calculated flank wear. The risk of exceeding the discard criterion is thus more limited than in prior art methods.

In a variant, the wear of the flank of the cutter tool, i.e. in this example calculating the maximum flank wear VBmax by means of the general function f, may be determined a posteriori. The magnitudes necessary for said calculation, such as the radial force Fr and the cutting energy Ec are nevertheless themselves measured in real time.

In another implementation, the characteristic length, e.g. the maximum flank wear VBmax, may be calculated in predictive manner, prior to machining, using a general function having arguments that do not depend on time. For example, the initiation and linear stages of variation in flank wear may be modeled by a first function f1 that depends on the length of cut Lc, and in particular a function of the following form:

$$f1(Vc, fz, Lc) = 10^{A1} Vc^{B1} fz^{C1} Lc^{D1}$$

where Vc is the cutting speed, fz is the feed per revolution and per tooth, Lc is the length of cut, and A1, E1, C1, and D1 are four constants. Surprisingly, the inventors have observed that the constants of this first function having as its argument the length of cut are of the same order of magnitude as the constants A1 to D1 of the first function having cutting energy as its argument. There therefore exists a physical correlation that justifies the operation of the predictive model even though, as mentioned above, flank wear depends on the machining history of the tool.

An implementation of the method of evaluating the wear of a flank of a cutter tool in another aspect of the invention is described below with reference to a cutter tool of the above-described type, as used for turning TA6V. It is chosen to characterize the wear of the flank of the cutter tool by the maximum flank wear VBmax. Nevertheless, the present invention applies not only to turning, nor only to TA6V, and it is possible to select some other length that is characteristic of the maximum flank wear VBmax.

While machining a part made by the cutter tool, measurements are made of the cutting force Fc exerted by the cutter tool on the part, the axial force Fx exerted by the cutter tool on the part, the radial force Fr exerted by the cutter tool on the part, the axial movement Dx of the cutter tool relative to the part, and the cutting movement of the cutter tool relative to the part. The variations in these five magnitudes as a function of time are shown in FIG. 6 for various values of the maximum flank wear of the cutter tool.

Figure 6:
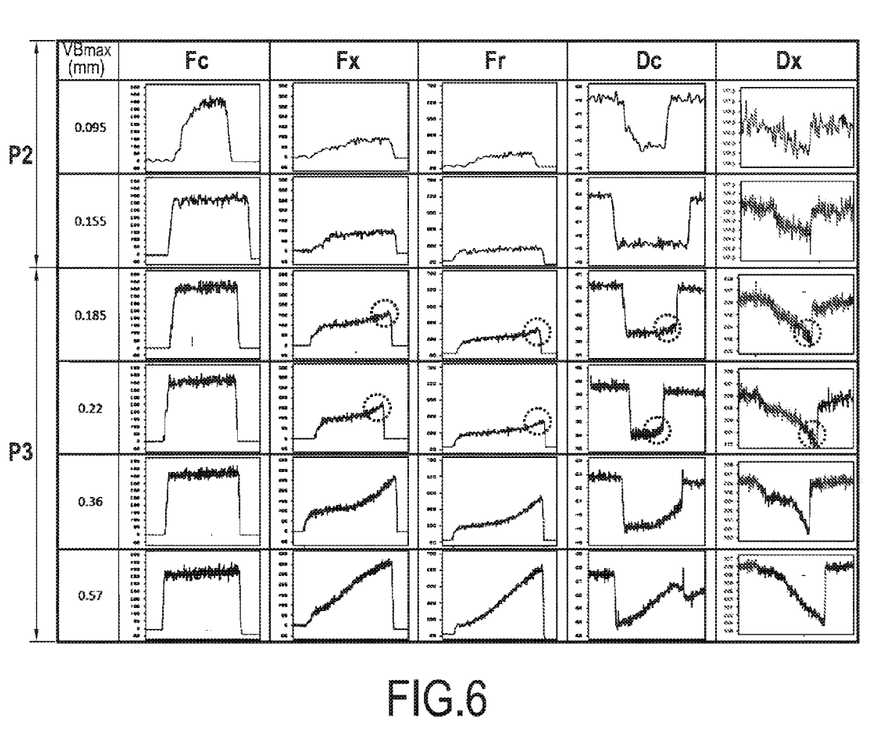
FIG. 6 shows a set of measurements of magnitudes for different values of maximum flank wear, in linear stages and in catastrophic stages.
Figure 7:
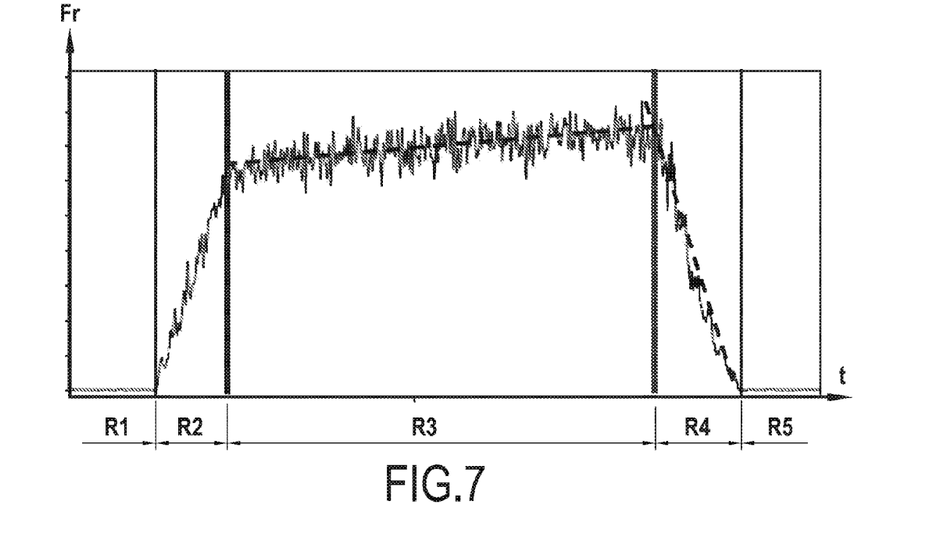
FIG. 7 shows various speeds of overall variation in a magnitude measured during machining, during the linear stage of wear of the cutter tool.

The measurement of magnitudes shown in FIG. 6 vary as a function of time under five successive regimes which are shown diagrammatically in FIG. 7 for the radial force Fr during the linear stage. A first regime R1 is a rest regime, in which the cutter tool is not in contact with the part. In this first regime R1, the forces Fc, Fx, and Fr exerted by the cutter tool on the part are zero and the movements Dc, Dx may be constants (ignoring vibration, if any). During a second regime R2, which is a transient regime, the cutter tool penetrates into the part until it reaches its cutting position. In a third regime R3, the cutter tool performs cutting proper; so long as the flank wear of the cutter tool is not in the catastrophic stage during the third regime R3, the magnitude varies regularly and without any sudden change. In particular, its overall variation may be substantially constant (cf. for example Dx). In a fourth regime R4, the cutter tool moves away from the part in order to become completely separated therefrom. The cutter tool thus reaches a fifth regime R5, which is a rest regime similar to the first regime R1. In FIG. 6, each graph represents the measurement of one respective magnitude during the succession of these five regimes.

After measuring magnitudes, the method may include an optional step of filtering or calculation on the basis of one or more of the measurements that have been obtained. This filtering or calculation step may in particular be a preprocessing step seeking to obtain the overall variation of the magnitude, or more generally to facilitate detecting a sudden change as is performed subsequently. This step may comprise applying a noise-reduction filter (lowpass filter) or any other type of transformation.

During the present method, the beginning of a catastrophic stage in the increase of flank wear of the cutter tool is determined by detecting a sudden change in the overall variation of at least one of the five above-mentioned magnitudes as a function of time. Insofar as the second and fourth regimes R2 and R4 are transient, the detection of said sudden change preferably takes place during the third regime R3.

Figure 8:
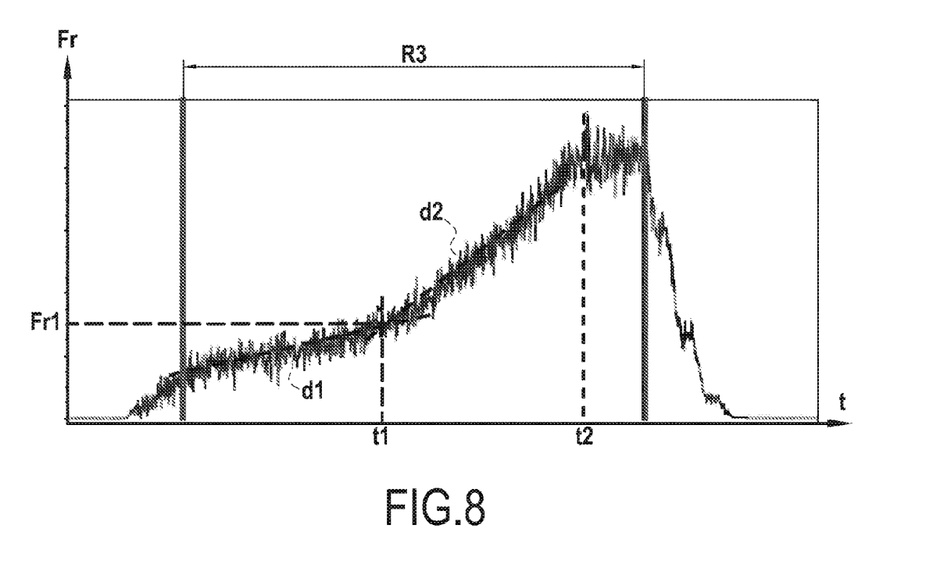
FIG. 8 shows detecting a sudden change in a measurement of a force during a catastrophic stage in the wear of the cutter tool.

In the present implementation, the search for the sudden change is a search for a point at which there is a break of slope. FIG. 8 shows an example of detecting such a slope breakpoint representing a sudden change in the overall variation of the radial force Fr and entry into the catastrophic stage. As shown by dashed straight lines d1 and d2, the curve representing variation in the radial force Fr during the regime R3 generally follows a first straight line d1 up to a time t1 and a second straight line d2 from the time t1 up to a time t2. The time t2 is the abscissa point for an extreme value of the radial force Fr, specifically a maximum value. The time t1 is the abscissa point at the point of intersection between the straight lines d1 and d2 and it defines the instant of the break of slope, thus the instant at which there is a sudden change in the variation of the radial force Fr.

The straight lines d1 and d2 represent the overall variation in the radial force Fr during the regime R3. These straight lines d1 and d2 may be established by any means available to the person skilled in the art, e.g. by linear regression. Other characteristics of the overall variation of the radial force could be used; in the present example, straight lines obtained by linear regression are particularly suitable for detecting a slope breakpoint.

In FIG. 6, for values of maximum flank wear VBmax that are strictly less than 0.185 mm, no sudden change is detected for the variations in the magnitudes. A sudden change can be seen to appear in the overall variations of the axial force Fx, of the radial force Fr, of the cutting movement Dc, and of the axial movement Dx as from VBmax=0.185 mm. For VBmax=0.185 mm and VBmax=0.22 mm, these sudden changes are marked more particularly by dotted circles. The beginning of a stage P3 of catastrophic increase in the wear of the flank of the cutter tool thus occurs as soon as VBmax=0.185 mm. Although this cannot be seen in FIG. 6, the sudden change can also be identified in the variation of the cutting force Fc for other types of machining.

In the present implementation, the beginning of the catastrophic stage P3 is detected on the basis of a sudden change in the overall variation of a single magnitude. Nevertheless, in a variant, for increased reliability, it is possible to confirm this detection by detecting a sudden change in the overall variation of a distinct second magnitude, and to determine that the catastrophic stage P3 has begun only from the moment when a sudden change has also been detected in the overall variation of the second magnitude.

In addition, although the present implementation is described with a sudden change corresponding to a slope breakpoint, other types of sudden change can be detected. When sudden changes are detected in the overall variations of at least two different magnitudes, there is no need for the detected sudden changes all to be of the same kind.

Although the present invention is described with reference to specific implementations, modifications may be made to these implementations without going beyond the general ambit of the invention as defined by the claims. In particular, individual characteristics of these various implementations shown and/or mentioned may be combined in additional implementations. Consequently, the description and the drawings should be considered in a sense that is illustrative rather than restrictive.

The invention claimed is:

1. A determination method for determining wear of a flank of a cutter tool, wherein said wear is determined with a general function calculating a characteristic length of said wear as a function of at least one variable representative of operating conditions of machining performed by the cutter tool, the method comprising:
    obtaining an operating condition of said operating conditions of the machining performed by the cutter tool;
    calculating a first value of said characteristic length of said wear by a first function;
    calculating a second value of said characteristic length of said wear by a second function;
    calculating said general function as a maximum value of said first value and said second value; and
    determining said wear of the flank of the cutter tool using said general function.

2. The determination method according to claim 1, wherein said wear is determined in real time.

3. The determination method according to claim 1, wherein at least one of the first function or the second function depends on constants determined by machining tests.

4. The determination method according to claim 1, wherein the characteristic length of the wear of the flank is calculated as a function of cutting speed, feed per revolution and per tooth, depth of cut, cutting energy, and radial force.

5. The determination method according to claim 1, wherein the first function depends on time t and the first function is of the form:

$$f1(Vc, fz, Ec, t) = 10^{A1} Vc^{B1} fz^{C1} Ecc^{D1}$$

where Vc is a cutting speed, fz is a feed per revolution and per tooth, Ecc is an accumulated cutting energy, and A1, B1, C1, and D1 are four constants.

6. The determination method according to claim 1, wherein the second function depends on time t, and the second function is of the form:

$$f2(Vc, fz, Fr, t) = 10^{A2} 10^{[B2 + C2 \, \log(fz) + D2 \, \log(Vc)] \cdot \log(Frc)}$$

where Vc is a cutting speed, fz is a feed per revolution and per tooth, Frc is an accumulated radial force, and A2, B2, C2, and D2 are four constants.

7. The determination method according to claim 1, wherein the first function depends on cutting length Lc and the first function is of the form:

$$f1(Vc, fz, Lc) = 10^{A1} Vc^{B1} fz^{C1} Lc^{D1}$$

where Vc is cutting speed, fz is a feed per revolution and per tooth, Lc is the cutting length, and A1, B1, C1, and D1 are four constants.

8. A non-transitory computer readable data medium including a computer program comprising instructions for executing steps of the determination method according to claim 1.

9. A device for determining wear of a flank of a cutter tool for machining a part, the device comprising:
    circuitry configured to determine a characteristic length of said wear, by taking account of at least one variable representative of operating conditions of machining performed by the cutter tool, wherein
    the circuitry is configured to:
    obtain an operating condition of said operating conditions of the machining performed by the cutter tool;
    calculate a first value of said characteristic length of said wear by a first function;
    calculate a second value of said characteristic length of said wear by a second function;
    calculate said characteristic length as a maximum value of said first value and said second value; and
    determine said wear of the flank of the cutter tool using said characteristic length.

10. The determination method according to claim 1, further comprising replacing the cutter tool when the characteristic length of the wear is greater than a predetermined threshold.

* * * * *

UNITED STATES PATENT AND TRADEMARK OFFICE
CERTIFICATE OF CORRECTION

PATENT NO. : 10,401,271 B2
APPLICATION NO. : 15/038200
DATED : September 3, 2019
INVENTOR(S) : Mickael Rancic et al.

It is certified that error appears in the above-identified patent and that said Letters Patent is hereby corrected as shown below:

On the Title Page

Item (71), the Applicant's name is incorrect. Item (71) should read:
-- (71) Applicant: SAFRAN AIRCRAFT ENGINES, Paris (FR) --

Signed and Sealed this
Tenth Day of December, 2019

Andrei Iancu
*Director of the United States Patent and Trademark Office*